United States Patent
Park et al.

(10) Patent No.: US 8,957,117 B2
(45) Date of Patent: Feb. 17, 2015

(54) METHANOL SYNTHESIS PROCESS

(75) Inventors: Colin William Park, Darlington (GB); Brian Peter Williams, Stockton on Tees (GB); Gordon James Kelly, Darlington (GB); Terence James Fitzpatrick, Middlesbrough (GB)

(73) Assignee: Johnson Matthey PLC, London (GB)

( * ) Notice: Subject to any disclaimer, the term of this patent is extended or adjusted under 35 U.S.C. 154(b) by 573 days.

(21) Appl. No.: 13/378,595

(22) PCT Filed: May 24, 2010

(86) PCT No.: PCT/GB2010/050844
§ 371 (c)(1),
(2), (4) Date: Mar. 19, 2012

(87) PCT Pub. No.: WO2010/146380
PCT Pub. Date: Dec. 23, 2010

(65) Prior Publication Data
US 2012/0165418 A1    Jun. 28, 2012

(30) Foreign Application Priority Data

Jun. 17, 2009 (GB) .................................. 0910366.4

(51) Int. Cl.
| | | |
|---|---|---|
| *C07C 27/00* | (2006.01) | |
| *B01J 23/80* | (2006.01) | |
| *B01J 23/00* | (2006.01) | |
| *C07C 29/154* | (2006.01) | |
| *B01J 23/72* | (2006.01) | |
| *B01J 35/00* | (2006.01) | |
| *B01J 35/02* | (2006.01) | |
| *B01J 37/18* | (2006.01) | |

(52) U.S. Cl.
CPC ................ *B01J 23/80* (2013.01); *B01J 23/002* (2013.01); *C07C 29/154* (2013.01); *B01J 23/72* (2013.01); *B01J 35/0026* (2013.01); *B01J 35/0053* (2013.01); *B01J 35/026* (2013.01); *B01J 37/18* (2013.01); *B01J 2523/00* (2013.01)
USPC ............................ 518/714; 518/700; 518/713

(58) Field of Classification Search
CPC ........ C07C 31/04; C07C 29/154; B01J 23/72; B01J 2523/22; B01J 2523/17; B01J 2523/27; B01J 2523/31

USPC ......................................... 518/700, 713, 714
See application file for complete search history.

(56) References Cited

U.S. PATENT DOCUMENTS

| | | | |
|---|---|---|---|
| 4,535,071 | A | 8/1985 | Schneider et al. |
| 4,863,894 | A | 9/1989 | Chinchen et al. |
| 6,919,066 | B2 | 7/2005 | Hölzle et al. |
| 7,387,983 | B2 | 6/2008 | Hölzle et al. |
| 2008/0033218 | A1 * | 2/2008 | Lattner et al. ................. 568/897 |

FOREIGN PATENT DOCUMENTS

| | | |
|---|---|---|
| EP | 0 125 689 A2 | 11/1984 |
| EP | 0 157 480 A2 | 10/1985 |
| EP | 0 202 824 A2 | 11/1986 |
| EP | 0 217 513 A1 | 4/1987 |
| EP | 0 296 734 A1 | 12/1988 |
| GB | 1010871 | 11/1965 |
| GB | 1159035 | 7/1969 |
| GB | 1 296 212 | 11/1972 |
| GB | 1 405 012 | 9/1975 |
| WO | WO-2008/047166 A2 | 4/2008 |
| WO | WO-2008/146032 A1 | 12/2008 |

OTHER PUBLICATIONS

Evans et al., "On the Determination of Copper Surface Area by Reaction with Nitrous Oxide," *Applied Catalysis*, 1983, vol. 7, pp. 75-83.
International Search Report dated Nov. 4, 2010, from International Application No. PCT/GB2010/050844.
International Preliminary Report on Patentability dated Dec. 20, 2011, from International Application No. PCT/GB2010/050844.

* cited by examiner

*Primary Examiner* — Jafar Parsa
(74) *Attorney, Agent, or Firm* — RatnerPrestia

(57) ABSTRACT

A methanol synthesis process includes reacting a process gas containing hydrogen, carbon dioxide and carbon monoxide over a catalyst including shaped units formed from a reduced and passivated catalyst powder the powder including copper in the range 10-80% by weight, zinc oxide in the range 20-90% by weight, alumina in the range 5-60% by weight and optionally one or more oxidic promoter compounds selected from compounds of Mg, Cr, Mn, V, Ti, Zr, Ta, Mo, W, Si and rare earths in the range 0.01-10% by weight, to form a product gas, and condensing methanol, water and oxygenate by-products therefrom, wherein the total oxygenate by-product level in the condensate is below 500 ppm.

21 Claims, No Drawings

METHANOL SYNTHESIS PROCESS

CROSS-REFERENCE TO RELATED APPLICATIONS

This application is the U.S. National Phase application of PCT International Application No. PCT/GB2010/050844, filed May 24, 2010, and claims priority of British Patent Application No. 0910366.4, filed Jun. 17, 2009, the disclosures of both of which are incorporated herein by reference in their entireties for all purposes.

FIELD OF THE INVENTION

This invention relates to a methanol synthesis process.

BACKGROUND OF THE INVENTION

Methanol synthesis is of considerable industrial importance. Methanol is typically synthesised in a synthesis loop over copper-containing catalysts from synthesis gases containing carbon monoxide and carbon dioxide. These reactions are depicted below.

$$CO + 2H_2 \rightarrow CH_3OH$$

$$CO_2 + 3H_2 \rightarrow CH_3OH + H_2O$$

The unreacted product gases are generally returned to the loop, from which a purge may be taken to prevent the build up of inerts.

The catalysts for such reactions are generally produced by forming into pellets small discrete particles of an intimate mixture of copper oxide and one or more other oxidic materials, generally including zinc oxide, that are not reduced under the conversion reaction process conditions. The intimate mixture is generally made by precipitation of copper compounds and compounds convertible to the other oxidic materials, and/or precipitation of the copper compounds in the presence of the other oxidic materials or compounds convertible thereto, followed by calcination to convert the precipitated copper compounds, and other components as necessary, to the oxides. Hence pellets are conventionally formed form oxidic powders. In order to generate the active catalyst, the pellets are subjected to reducing conditions to reduce the copper oxide in said pellets to metallic copper. The reduction step is normally carried out in the reactor where the methanol synthesis process is to be effected: thus normally a catalyst precursor in which the copper is present in the form of copper oxide is charged to the reactor and the reduction effected by passing a suitable gas mixture there-through. The reduction of copper oxide is exothermic and the in-situ reduction step is often carried out over extended periods using dilute hydrogen streams to avoid damaging the catalyst. Such extended start-up procedures are difficult to control and can be costly to operate.

By such precipitation/calcination/reduction techniques, the catalysts generally have a copper surface area above 20 m² per gram of copper, often above 40 m² per gram of copper. Commercially available carbon oxide conversion catalysts typically have a copper surface area about 50 m²/g per gram of copper. Copper surface area may be measured by the nitrous oxide decomposition method, e.g. as described in the article by Evans et al. in *Applied Catalysis* 1983, 7, 75-83 and a particularly suitable technique is described in EP 0202824.

Since the activity of the catalysts is linked to the copper surface area, it is desirable to obtain catalysts with higher copper surface areas.

U.S. Pat. No. 4,863,894 describes a process for the manufacture of a catalyst comprising forming a composition comprising an intimate mixture of discrete particles of compounds of copper, and zinc and/or magnesium and, optionally, at least one element X selected from aluminium, vanadium, chromium, titanium, zirconium, thorium, uranium, molybdenum, tungsten, manganese, silicon, and the rare earths, and subjecting the composition to reduction conditions so that the copper compounds therein are converted to copper, wherein the copper compounds in the intimate mixture are reduced to metallic copper without heating said intimate mixture to a temperature above 250 DEG C. The direct reduction of the precipitated catalyst precursor compositions, rendered catalysts having copper surface areas >70 m² per gram copper.

However copper surface area is not the only criterion that needs to be taken into account for carbon oxides conversion catalysts. In particular, catalyst strength and stability, both in terms of activity and selectivity, are also important. The catalysts obtained by the process of U.S. Pat. No. 4,863,894 do not have the high stability required in modern carbon oxides conversion processes, and currently oxidic catalysts are still used.

SUMMARY OF THE INVENTION

We have found surprisingly that a process using shaped catalyst formed from a reduced and passivated catalyst powder is able to provide higher methanol selectivities that the conventional catalysts.

Accordingly the invention provides a methanol synthesis process comprising the steps of
  (i) reacting a process gas containing hydrogen, carbon dioxide and carbon monoxide over a catalyst comprising shaped units formed from a reduced and passivated catalyst powder said powder comprising copper in the range 10-80% by weight, zinc oxide in the range 20-90% by weight, alumina in the range 5-60% by weight and optionally one or more oxidic promoter compounds selected from compounds of Mg, Cr, Mn, V, Ti, Zr, Ta, Mo, W, Si and rare earths in the range 0.01-10% by weight, to form a product gas, and
  (ii) condensing methanol, water and oxygenate by-products therefrom,
  wherein the total oxygenate by-product level in the condensate is below 500 ppm.

It will be understood that the total oxygenate by-product level does not include condensed water or the methanol product. The total oxygenate level may readily be established using conventional techniques, such as gas chromatography, using known standards. The total oxygenate by-product level may be the total organic oxygenate level measured but is usefully considered to be the sum of the ppm weight of ethanol, 2-propanol, 1-propanol, methyl ethyl ketone, 2-butanol, 2-methyl propan-1-ol and 1-butanol in the recovered condensate.

Whereas the total oxygenate by-product level in the process is <500 ppm, it is possible to obtain a total oxygenate by-product level below 400 ppm, preferably below 300 ppm using the present invention.

Ethanol is the largest oxygenate by-product. Preferably the ethanol content of the condensate is ≤300 ppm, preferably ≤250 ppm.

The relative condensate purity may also be considered a useful measure of the selectivity of the current process. The relative purity may be established by measuring the total oxygenate by-product level of a catalyst comprising the same molar ratio of Cu, Zn, Al and other components prepared by reduction of shaped units formed from an oxidic catalyst precursor as opposed to shaped units formed from a reduced and passivated precursor prepared as described herein. The relative condensate purity in the process of the present invention may be expressed as a percentage of the total oxygenate by-product level in the condensate produced in the process of the present invention to that of the 'oxidic catalyst process' using a catalyst of the same composition. The relative condensate purity obtained in the present process is ≤75%, preferably ≤50%, i.e. the process of the present invention produces ≤75%, preferably ≤50% of the amount of oxygenate by-products in the condensate than an equivalent 'oxide catalyst process'.

Thus the invention includes a methanol synthesis process comprising the steps of:
(i) reacting in a synthesis loop a process gas containing hydrogen, carbon dioxide and carbon monoxide over a catalyst comprising shaped units formed from a reduced and passivated catalyst powder said powder comprising copper in the range 10-80% by weight, zinc oxide in the range 20-90% by weight, alumina in the range 5-60% by weight and optionally one or more oxidic promoter compounds selected from compounds of Mg, Cr, Mn, V, Ti, Zr, Ta, Mo, W, Si and rare earths in the range 0.01-10% by weight, to form a product gas, and
(ii) condensing methanol, water and oxygenate by-products therefrom,
wherein the relative condensate purity is ≤75%, preferably ≤50%.

DETAILED DESCRIPTION OF THE INVENTION

The process of the present invention is particularly useful because it offers faster start-up than conventional oxidic catalysts, offers higher activity and increased selectivity in methanol production, which is of considerable benefit in modern large-scale facilities as it improves productivity and reduces waste streams.

The copper content (expressed as Cu atoms) of the active catalyst is typically in the range 10-80%, preferably 15-70%, by weight. Within this range a copper content in the range 50-70% by weight is of particular suitability for methanol synthesis. In the catalyst, the copper will be present in an oxidised form in the passivation layer and in elemental form beneath this layer. Preferably in the catalyst as made <50% (by atoms) more preferably <40% (by atoms) of the copper is in oxidised form.

In addition to metallic copper, the catalyst can contain one or more other metals having catalytic activity: where the process is alcohol synthesis, examples of such other metals are cobalt, palladium, rhodium, or ruthenium. Optionally metallic silver can be present. Other catalytically active metals, if present, are normally present in relatively low proportions; the proportion of such other catalytically active metals is typically 1-10 atoms of such metals per 100 atoms of copper.

Copper containing catalysts suffer from the problem that, upon heating above about 250° C., the copper atoms tend to sinter together giving a decrease in the copper surface area after a period of use at elevated temperature with consequent loss of activity. In order to alleviate this disadvantage, the catalyst contains at least one further material, including zinc compounds and optionally one or more compounds selected from compounds of Mg, Cr, Mn, V, Ti, Zr, Ta, Mo, W, Si and rare earths. In the catalyst, the zinc oxide content may be in the range 20-90% by weight, and the one or more oxidic promoter compounds, if present, may be present in an amount in the range 0.01-10% by weight. Magnesium compounds are preferred and the catalyst preferably contains magnesium in an amount 1-5% by weight, expressed as MgO. The promoter compounds are not reduced to metal under the process conditions and are typically present as one or more oxides in the catalyst.

Aluminium in the form of aluminium oxide, including partially hydrated aluminium oxide, is also present in the catalyst. The amount of aluminium oxide may be in the range 5-60% by weight (expressed as $Al_2O_3$). The aluminium oxide may be included directly or formed from aluminium compounds that decompose to the oxide or hydrated oxide.

A preferred catalyst precursor composition comprises, prior to reduction, a solid containing mixed metal carbonates, including hydroxycarbonates, of Cu and Zn, with alumina or hydrated alumina dispersed therein and optionally containing one or more Mg, Cr, Mn, V, Ti, Zr, Ta, Mo, W, Si or rare earths compounds, particularly Mg compounds, as a promoter. The catalyst preferably contains 30-70% wt copper (expressed as CuO). The weight ratio of Cu:Zn (expressed as CuO:ZnO) may be 1:1 or higher but is preferably is in the range 2:1 to 3.5:1 by weight for alcohol synthesis catalysts.

Particularly preferred catalyst compositions suitable for methanol synthesis have molar ratios of Cu:Zn:Mg:Al in the ranges 16.5 to 19.5:5.5 to 8.5:1.0 : 2.5 to 6.5.

As mentioned above, copper-containing catalysts are conventionally prepared by forming an intimate mixture of particles of compounds of copper, and zinc, calcining the mixture, often in an oxygen-containing atmosphere, usually air, to convert those compounds to oxides, followed by pelleting, and then reduction. The calcination is normally effected at temperatures in an excess of 275° C. and is generally effected at temperatures in the range 300 to 500° C.

Preferably, the catalyst used in the present invention is prepared by steps comprising:
(i) forming, in an aqueous medium, a composition comprising an intimate mixture of discrete particles of compounds of copper, zinc, aluminium and optionally one or more promoter metal compounds selected from compounds of Mg, Cr, Mn, V, Ti, Zr, Ta, Mo, W, Si and rare earths,
(ii) recovering and drying the composition to form a catalyst precursor,
(iii) subjecting the dried catalyst precursor composition to reduction conditions so that the copper compounds therein are converted to copper,
(iv) passivating the reduced copper surfaces, and
(v) shaping the reduced and passivated composition,
wherein, prior to the reduction of the copper compounds, the intimate mixture is subjected to a drying step at a temperature in the range 180-240° C.

In the present invention, in order to obtain high activity, the calcination step is omitted, and the dried intimate mixture is subjected to reduction conditions so that the copper compounds therein are converted to copper without an initial discrete step of heating to convert the copper compounds to copper oxide. Rather, the drying is carefully controlled to ensure that the water is driven off as completely as is possible without causing the decomposition of the copper compounds to copper oxide.

The copper surface areas of the catalysts are desirably ≥60 $m^2$/g Cu, and are preferably ≥70$m^2$/g Cu, more preferably ≥75$m^2$/g Cu, most preferably ≥80$m^2$/g Cu. As stated above the copper surface area may be readily established by using reactive frontal chromatography as described in EP-A-202824. A particularly suitable method is as follows; Catalyst shaped units are crushed and sieved to particle size of 0.6-1.00mm. About 2.0 g of the crushed material is weighed into in a glass tube and heated to 30° C. (for reduced and passivated samples) or 68° C. (for oxidic samples) and purged with helium for 2 minutes. Then the catalyst is reduced by heating it in a flow of 5% vol $H_2$ in helium, at 4° C./min up to 230° C. and then holding it at this temperature for 30 minutes. Catalyst is then cooled to 68° C. under Helium. The reduced catalyst then has 2.5% vol $N_2O$ in helium passed over the catalyst. The evolved gases are passed through a gas chromatograph and the $N_2$ evolution is measured. From this the copper surface area of the catalyst may be calculated.

The crush strength ratio of the catalyst shaped units, which is the ratio of the mean horizontal crush strength (in kilograms) of the reduced shaped unit to the mean horizontal crush strength (in kilograms) of the catalyst shaped unit as made is desirably ≥0.500:1, preferably ≥0.600:1, more preferably ≥0.650:1, most preferably ≥0.700:1, especially ≥0.750:1. Measurement of the ratio requires a measurement of the crush strength of the catalyst shaped units as made, i.e. the shaped units formed from the reduced and passivated powder, and also on the re-reduced shaped unit, i.e. of the shaped units once the copper passivation layer has been re-converted to elemental copper by exposure to a reducing gas stream. Hence, the strength of the catalyst shaped units as made may be performed on the reduced and passivated catalyst in air whereas the strength of the re-reduced catalyst is desirably measured under an inert atmosphere to prevent exothermic oxidation of the shaped unit. The crush strength of the catalyst as-made, expressed as the mean horizontal crush strength, is preferably ≥6.5 kg more preferably ≥10.0 kg most preferably ≥12.0 kg so that the catalyst has sufficient strength to be loaded into the reactor for the carbon oxides conversion process. The mean horizontal crush strengths (MHCS) may be determined using conventional techniques. A suitable method for the as-made shaped units is as follows. Crush strength of the shaped units are measured on cylindrical pellets using a calibrated CT5 pellet strength testing machine. Pellet crush strengths are measured in the horizontal (i.e. radial) plane. A 50 kg load cell is used and the crush strength speed is 2.5 mm/min. At least 20 pellets are tested and the average figure quoted. For measuring the crush strengths on reduced pellets, the oxidic or reduced and passivated pellets must first be subjected to a reduction step. This may be achieved by placing the pellets in a vessel, purging the air with nitrogen and then exposing the pellets to 2% $H_2$ in nitrogen and heating to 90° C. over 2 hours, then to 120° C. over a further 2 hours, then to 180° C. over a further 5 hours and then 235° C. over a further 7 hours, holding at 235° C. for 3 hours, then heating to 240° C. over a further 1 hour and then holding at 240° C. for 3 hours before cooling in the presence of the reducing gas and purging with nitrogen for storage. The reduced pellets are and tested under an inert (i.e. $O_2$-free) atmosphere using the CT 5 equipment located in a glove-box.

Since there is no calcination step prior to reduction, the intimate mixture is not shaped prior to reduction because the intra-pellet voidage resulting from the decomposition of e.g. hydroxycarbonate compounds, during which water and/or carbon dioxide is evolved, can result in low mechanical strength and thus short process life.

The intimate mixture can be made by wet treatment of oxides, such as by reacting copper oxide, zinc oxide, and ammonia together in an aqueous medium such as water, or by mixing soluble metal compounds. More conveniently, it is made by decomposition of metal nitrates with an alkaline precipitant in an aqueous medium such as water, for example as described in GB-A-1010871, GB-A-1159035, GB-A-1296212 and GB-A-1405012. The reaction and after-treatment conditions of the resulting slurry can be chosen to produce definite crystalline compounds for example of the Manasseite, Rosasite, Aurichalcite or Malachite type. A suitable procedure comprises co-precipitating soluble salts of the metals with a precipitant such as an ammonium, or alkali metal, hydroxide, carbonate or bicarbonate. The order in which the reactants are mixed may be optimised following known principles, for example employing single-stage co-precipitation as in GB-A-1159035 or 2-stage co-precipitation as in GB-A-1296212 and GB-A-1405012. Preferably all the divalent oxide constituents are introduced by such co-precipitation.

In a preferred embodiment, insoluble copper compounds and one or more other insoluble metal compounds are precipitated by combining an aqueous solution of one or more soluble metal compounds, such as a metal nitrate, sulphate, acetate, chloride or the like, and an aqueous solution of an alkaline carbonate precipitant, such as sodium or potassium carbonate. Non-carbonate precipitants may also be present such as alkali metal hydroxides or ammonium hydroxide. Hence, the intimate mixture of discrete particles may be formed by combining aqueous solutions of soluble metal compounds of copper, zinc and optionally one or more promoter metal compounds selected from compounds of Mg, Cr, Mn, V, Ti, Zr, Ta, Mo, W, Si or rare earths, with an aqueous solution of an alkaline carbonate precipitant in the presence of an alumina or hydrated alumina, or an aluminium compound decomposable thereto. In a preferred embodiment, a colloidally-dispersed aluminium oxide or aluminium hydroxide is used as the source of alumina. Such colloidally-dispersed aluminium oxides or aluminium hydroxides are commercially available or may be prepared using known methods. Their use in preparing copper catalysts is described, for example, in U.S. Pat. No. 4,535,071. Upon combining the metal solution and precipitant solution, the alkaline carbonate reacts with the soluble metal compound forming an insoluble metal carbonate, including metal hydroxy-carbonate. Ageing of the precipitated material may be carried out in a batch or semi-continuous procedure whereby the aqueous slurry of the precipitated material held at elevated temperatures in one or more stirred vessels for selected periods of time. Suspension of the compounds in the liquid can be by mere stirring, the vigour of stirring depending on the tendency of the particles to settle. If desired, a polymer can be present in solution to inhibit settling. Alternatively the precipitated material may be aged in a pulse-flow reactor as described in our WO2008/047166, which is herein incorporated by reference.

After such mixing, the intimate mixture is desirably recovered, e.g. by separation of the mother liquors using known methods such as filtering, decanting or centrifuging, and washed to remove soluble salts. Especially when alkali metal compounds are present, the alkali content should desirably be reduced to below 0.2% wt, preferably below 0.1% wt, more preferably below 0.05% wt calculated as the respective alkali metal oxide on the dried material.

After any washing, the material may be dried to form a catalyst precursor powder. In one embodiment the drying includes a stage performed at a maximum temperature in the range 180-240° C. The drying may therefore comprise heating the damp mixture in discrete stages or continuously over an extended period until the maximum temperature is reached. Preferably the drying step is performed using two or more distinct drying steps that remove the water in stages. The drying step may be performed using conventional drying equipment, such as that used for the oxidic catalysts. In one embodiment drying comprises an initial step of heating the damp intimate mixture to a temperature in the range 90-150°

C., preferably 100-125° C. under air or an inert gas in an oven, rotary drier or similar equipment. In an alternative embodiment, the initial drying step is performed using a spray-drier, which also acts to generate agglomerates of the intimate mixture particularly suitable for compression shaping into pellets. To facilitate spray drying, the washed material is desirably dispersed in water. The solids content of the spray drier feed may be above 15% by weight but is preferably ≥20% by weight. Conventional sprayer equipment may be used with an inlet temperature in the range 150-300° C., and an out let temperature in the range 100-200° C. In circumstances where the inlet temperature is above 240° C., the feed rate should be controlled so that the copper compounds suffer substantially no thermal decomposition. Spray-dried agglomerates with an average particle size (as determined by sieve fractions, i.e. the weight-average particle size) in the range 10-300 μm (microns) are preferred, particularly 100-250 μm.

Initial drying, whether by oven or spray drying, desirably reduces the water content of the catalyst precursor to <20% wt, preferably <15% wt, more preferably 10% wt.

Whether subjected to a one-step drying process or a discrete number of drying steps, the intimate mixture is desirably subjected to a drying step in which it is heated to a temperature in the range 180-240° C. Without wishing to be bound by theory, it is believed that drying at these temperatures removes the chemisorbed as well as physisorbed water form the catalyst precursor and that this renders a catalyst precursor with increased strength. The time it is held at the temperature in this range depends on the temperature chosen, with more extended periods desirable for lower temperatures in the range and shorter periods for higher temperatures. Drying times in the range 2 to 8, preferably 2 to 6 hours are desirable. The drying step may be performed in air or an inert gas, such as nitrogen or argon in an oven, rotary drier or other conventional drying equipment. As stated above, the drying step does not convert the copper compounds, e.g. copper hydroxycarbonate compounds, to copper oxide. After drying, the catalyst precursor is desirably stored under de-humidified air or dry inert gas to prevent re-adsorption of atmospheric water.

Reduction of the copper compounds may conveniently be achieved by exposing the dried catalyst precursor to a hydrogen- and/or carbon monoxide containing gas at atmospheric or elevated pressure. Reduction is carried out preferably at the lowest temperature at which it will proceed. Thus conventional hydrogen reduction techniques may be used wherein a dilute hydrogen stream, e.g. 2% $H_2$ in $N_2$ is used and the catalyst precursor heated slowly until reduction commences. Generally it is found that reduction begins at about 80° C. and is sufficiently complete by 200° C. or even 150° C.

In the present invention, we have observed that reduction of catalyst precursors containing copper carbonate compounds, such as copper hydroxycarbonate (malachite) and/or zincian malachite, may be performed with high concentrations of hydrogen in the reducing gas stream for the entire reduction stage without the problems normally observed in the reduction of copper-oxide containing materials. In a preferred embodiment therefore, reduction of catalyst precursors containing copper hydroxycarbonate materials is performed by exposing the dried catalyst precursor to hydrogen-containing gas streams comprising >50% vol hydrogen, more preferably >75% vol hydrogen, especially >90% vol hydrogen. If desired, substantially pure hydrogen may even be used.

The reduction may be performed until no further water and carbon dioxide are evolved from the catalyst precursor. The reduction normally converts at least 50% of the reducible compounds, e.g. copper carbonates, to metal but is preferably continued until >95% of the reducible compounds are converted to metal. The zinc and promoter compounds are largely converted to their respective oxides during the reduction stage.

In the reduced state, because of the high surface area, the copper may rapidly and exothermically react with oxygen and moisture present in the air and so it has to be passivated for shaping and storage. The composition is considered passivated when it is stable to air, particularly air at temperatures >50° C. This may be determined by thermogravimetric analysis (TGA) in which the weight change of the material is monitored as it is heated. As oxidation occurs, the catalyst increases in weight. Desirably, the passivated catalyst shows no substantial weight gain when heated in air at 20° C./min until the temperature has reached at least 80° C., preferably at least 90° C.

Passivation may be performed using dilute oxygen and/or carbon dioxide or the catalyst precursor powder may be coated with an oxygen barrier material. Passivation may be achieved by using inert gas/air mixtures, such as nitrogen/air mixtures, whereby the air concentration is slowly increased over a period in order to generate a thin metal oxide layer on the copper surfaces. Typically oxygen is introduced using air at a rate sufficient to maintain the temperature of the catalyst precursor at between 10 and 100° C., preferably 10 and 50° C., especially 20-40° C. during the passivation. For example the reduced material may be exposed to an inert gas, e.g. nitrogen, flow and air added at 0.1% vol. This is carefully increased over a period of time to 0.5% vol oxygen, then 1% vol, then 2% vol, 5% vol and so on until the oxygen content is that of air. Alternatively, reduced catalyst compositions may be passivated using a gas mixture comprising carbon dioxide and oxygen with a $CO_2:O_2$ ratio ≥2:1 in order to form a thin layer of a metal carbonate, e.g. a metal hydroxycarbonate, on the surface.

The reduced and passivated catalyst precursor powder can then be further processed to give shaped units, inter alia the following steps being possible:
(i) Pre-compaction and pelleting of the reduced and passivated powder, such that the shaped units are pellets,
(ii) Combination of the reduced and passivated powder with one or more binders, and optionally one or more further powder materials and tumbling to form spherical agglomerates or granules,
(iii) Conversion of the reduced and passivated powder into a slurry (preferably non-aqueous), kneading/grinding in a pan mill and extrusion to form extrudates.
(iv) Conversion into a slurry as above, kneading/grinding in a pan mill and extrusion to give complex mouldings, such as monolithic structures or catalyst plates with or without secondary structure.
(v) Application of the reduced and passivated powder to inert or likewise catalytically active supports by means of wash-coating or similar processes.

In all processes, the use of binders and additives common in the art may be used. Numerous other possibilities for further processing are also possible.

Pre-compaction and pelleting of the powder is most suitable for preparing shaped units. The pellet may be the conventional flat-ended cylindrical pellet. Cylindrical pellets for carbon oxide conversion processes suitably have a diameter in the range 2.5-15 mm, preferably 3-10 mm and an aspect ratio (length/diameter) in the range 0.5-2.0 . Alternatively, the shaped unit may be in the form of rings or trilobes. In a preferred embodiment the shaped unit is in the form of a domed cylinder having two or more grooves running along its length. In one such embodiment, the catalyst is in the form of a cylinder having a length C and diameter D, wherein the exterior surface of the unit has two or more flutes running along its length, said cylinder having domed ends of lengths A and B such that (A+B+C)/D is in the range 0.50 to 2.00, and (A+B)/C is in the range 0.40 to 5.00. A and B are preferably the same. C is preferably in the range 1 to 25 mm, D is preferably in the range 4 to 40 mm, more preferably 4 to 10 mm, and most preferably there are 4-flutes evenly spaced around the cylinder. Alternatively, or in addition, the shaped units may have one or more through-holes extending therethrough. Such highly domed cylindrical catalysts have improved packing and/or lower pressure drop than conventional non-fluted or non-holed shapes. Such adaptation of the conventional flat-ended cylindrical catalyst shape has been made possible by the improved strength properties of the reduced and passivated catalyst precursor powder.

Pellets, particularly cylindrical pellets with flat or domed ends as described above, are desirably made with pellet densities in the range 1.4 to 2.5 g/cm$^3$, more preferably 1.8 to 2.4 g/cm$^3$. The pellet density may readily be determined by calculating the volume from the pellet dimensions and measuring its weight. As the density is increased, the interstitial volume in the shaped units is reduced, which in turn reduces the permeability of reacting gases into and out of the unit. Therefore for densities >2.5 g/cm$^3$ the reactivity of the catalyst may be less than optimal, despite the high copper surface area of the reduced and passivated powder. For densities <1.4 g/cm$^3$ the crush strengths may be insufficient for long-term use in modern carbon-monoxide conversion processes.

The BET surface area of the catalyst, as determined by nitrogen absorption is desirably >80 m$^2$/g, more desirably >90 m$^2$/g; and the pore volume, as determined using the desorption branch at 0.99, is desirably >0.15 cm$^3$/g, more desirably >0.2 cm$^3$/g.

The catalyst may be placed in a conventional methanol reactor, i.e. as a fixed bed, although the size of the converter may be reduced as the process of the present invention is capable of producing a higher methanol yield in view of the higher activity and selectivity of the catalyst.

The catalyst may be pre-activated in-situ by exposing it to a reducing gas stream, preferably comprising hydrogen, to convert the passivated copper layer back into elemental copper. Thus the invention preferably includes the steps of (i) activating a catalyst comprising shaped units formed from a reduced and passivated catalyst powder said powder comprising copper in the range 10-80% by weight, zinc oxide in the range 20-90% by weight, alumina in the range 5-60% by weight and optionally one or more oxidic promoter compounds selected from compounds of Mg, Cr, Mn, V, Ti, Zr, Ta, Mo, W, Si and rare earths in the range 0.01-10% by weight, by contacting said catalyst with a reducing gas stream and (ii) exposing the reduced catalyst to a process gas containing hydrogen, carbon dioxide and carbon monoxide to form a product stream. Because the bulk of the copper is already in metallic form this activation step may be performed more quickly and with less water-by-product to be removed than with conventional copper oxide-containing catalysts. Activation may be performed using a hydrogen containing gas, including synthesis gas comprising hydrogen and carbon oxides, at temperatures above 80° C. and at pressures in the range 1-50 bar g. Again the maximum reduction temperature is desirably 150 to 200° C.

Typically methanol synthesis is performed in a loop with unreacted product gas, after condensate removal, and optionally after one or more further stages of methanol synthesis, mixed with make-up gas comprising hydrogen and carbon oxides in the desired ratio and returned to the methanol reactor.

A purge gas stream may be removed from any such loop to prevent the undesirable build up of inert/unreactive gases. If desired methanol may also be synthesised from this purge gas, or hydrogen recovered from it to adjust the stoichiometry of the feed gas or to generate power. The invention provides methanol synthesis processes using the catalyst, in particular:

A. Methanol synthesis in which a gas mixture containing carbon monoxide, hydrogen and optionally carbon dioxide, is passed over the catalyst at a temperature in the range 200-320° C., a pressure in the range 20-250, especially 30-120, bar abs and a space velocity in the range 500-20000 h$^{-1}$. The process can be on a once-through, or a recycle, basis and can involve cooling by indirect heat exchange surfaces in contact with the reacting gas, or by subdividing the catalyst bed and cooling the gas between the beds by injection of cooler gas or by indirect heat exchange. For this process the catalyst preferably contains copper, zinc oxide and magnesia, with alumina.

B. Modified methanol synthesis in which the catalyst contains also free alumina of surface area 50-300 m$^2$ g$^{-1}$, so that the synthesis product is relatively rich in dimethyl ether. Temperatures, pressures and space velocities are similar to those for methanol synthesis but the synthesis gas contains hydrogen and carbon monoxide in a molar ratio of less than 2.

In either case, the methanol synthesis may be part of a multiple synthesis process where the product gas, after the condensate has been removed, is fed to one or more further methanol synthesis reactors, which may contain the same or different methanol synthesis catalyst.

Synthesis gas compositions in the loop preferably have $P_{H2} > 2P_{CO} + 3P_{CO2}$ such that there is excess hydrogen to react with the oxides of carbon by the following reactions;

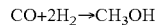

$$CO + 2H_2 \rightarrow CH_3OH$$

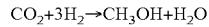

$$CO_2 + 3H_2 \rightarrow CH_3OH + H_2O$$

The stoichiometry number, R, as defined by R=(H$_2$—CO$_2$)/(CO+CO$_2$), of the synthesis gas in the loop fed to the catalyst, is preferably ≥3, more preferably ≥4, most preferably ≥5.

EXAMPLES

The invention will now be further described by reference to the following Examples.

Copper surface area and mean horizontal crush strength were measured using the methods described above. Crush strengths were measured using a CT5 desktop automatic mechanical strength tester (manufactured by Engineering Systems (Nottingham) Ltd).

Pellet shrinkage was measured by hand using digital callipers. Pellets before and after reduction were physically measured for volume changes. The reduced pellets were examined in a glove-box under an inert (i.e. O$_2$-free) atmosphere. 20-50 pellets were examined and an average is quoted.

Example 1

Catalyst Preparation

A catalyst precursor powder was prepared with the molar ratio Cu:Zn:Mg:Al of 17.5:6.5:1:4 by precipitating at 60-75° C. and a pH above 6.0, an intimate mixture from solutions of copper, zinc and magnesium nitrates in the presence of a colloidally-dispersed aluminium hydroxide sol, using potassium carbonate as precipitant. Once the co-precipitation had been completed the slurry was aged at 65° C. until the colour transition from blue to green occurred. The slurry was then filtered and washed until the alkali levels were at a minimum level (<500 ppm).

The resultant filter cake was then re-slurried to achieve a 35% w/w slurry and then spray-dried to form agglomerates of about 10-50 μm in diameter.

The spray-dried powder was then subjected to a drying step by heating it to 210-240° C. and maintaining it at this temperature for 6 hours. XRD analysis confirmed the presence of copper hydroxycarbonate and showed no formation of copper oxide during the drying step. The catalyst precursor material was then cooled to 60-80° C. in dry nitrogen.

The catalyst precursor was reduced by exposing it to a hydrogen-containing gas comprising >90% $H_2$, initially at about 80° C. with reduction performed at a maximum temperature of 160° C. The reduction process was continued until water and carbon dioxide were no longer evolved as measured using conventional detectors. Calculations indicated >95% of the copper was converted to elemental form. The reduced catalyst material was then cooled to 20-40° C. under dry nitrogen.

The reduced catalyst material was then passivated at 20-40° C. using nitrogen/air mixtures controlled initially to provide 0.1% vol oxygen and then increased gradually to 1% vol oxygen and then higher amounts until the passivating gas was 100% air. The rate of increasing the oxygen content was controlled by monitoring the temperature.

The passivated catalyst powder was mixed with a little graphite and shaped into cylindrical pellets using conventional pelleting equipment in air. The pellets were 5.4 mm diameter by 3.2 mm in length.

In comparison, a comparative catalysts having the same Cu:Zn:Mg:Al molar ratio, were prepared by the same precipitation process and spray dried using the same spray-drying method but instead of a high-temperature drying step, the spray-dried powders were subjected to a calcination at (I) 295° C. or (II) 500° C. wherein the copper compounds were converted to copper oxide. The resulting oxidic powders were again mixed with a little graphite and shaped into cylindrical pellets of 5.4 mm diameter by 3.2 mm length.

The copper surface areas of the pellets were determined by reactive frontal chromatography as described above. In each case the surface areas were measured on crushed and sieved pellets. The results were as follows;

| Sample | Copper surface area $m^2$/g Cu |
|---|---|
| Comparative material I (calcined 295° C.) | 40.0 |
| Comparative material II (calcined 500° C.) | 38.8 |
| Example 1 | 89.6 |

The results show that the copper surface areas of the reduced and passivated catalyst in accordance with the present invention are superior to those wherein the preparation includes a calcination step.

The MHCS was determined on the pellets as made and also following a reduction to simulate the strength in-situ.

| Pelleted material | Pellet Density g/cm³ | MHCS pellets as made (kg) | MHCS Reduced pellets (kg) | MHCS Ratio (Reduced:as made) |
|---|---|---|---|---|
| Comparative Catalyst I | 1.97 | 12.2 | 2.4 | 0.197:1 |
| Comparative Catalyst II | 1.97 | 8.4 | 2.6 | 0.310:1 |
| Example 1a | 2.04 | 17.2 | 14.3 | 0.831:1 |

The results show that very high crush strengths maybe achieved and that at comparable density, the pellets made from a precursor powder made with a calcination step are surprisingly weaker post-reduction than those used in the process of the present invention.

Example 2

The catalyst preparation of Example 1 was repeated.
The spray drier feed had a solids content of 20-35% wt.
Spray Drier settings were:
Inlet Temperature: 280-300° C.
Outlet temperature: 110-120° C.
Pump Pressure: 18-20 bar
Residual moisture of the spray-dried powder was <5-10%. 95% wt of the particles had a particle size 63-250 μm (microns).

The spray-dried product was subjected to the same drying step, reduction and passivation as Example 1. The reduced and passivated powder was formed into;
  a) cylindrical pellets with diameter 5.4 mm and length 3.2 mm and a pellet density of 1.73,
  b) highly-domed, 4-lobed/fluted cylindrical pellets with diameter 6.0 mm and total length 4.0 mm and a pellet density of 1.82 g/cm³. The top and bottom dome height was 1.5 mm, and
  c) highly-domed, 4-lobed/fluted cylindrical pellets with diameter 5.0 mm and total length 4.0 mm and a pellet density of 1.83 g/cm³. The top and bottom dome height was 0.5 mm.

The copper surface area was measured using the above method.

| Sample | Copper surface area $m^2$/g Cu |
|---|---|
| Example 2a | 80.1 |
| Example 2b | 75.8 |
| Example 2c | 78.3 |

A range of pellet densities was also explored for material 2a. The MHCS was determined on the pellets as made and also following a re-reduction to simulate the strength in-situ. The results were as follows.

| Sample | Pellet Density (g/mL) | MHCS As-Made (kg) | MHCS Re-reduced (kg) | MHCS Ratio | Shrinkage on Reduction (% v/v) |
|---|---|---|---|---|---|
| Example 2a | 1.73 | 8.8 | 6.9 | 0.784:1 | 11.2 |
| Example 2a' | 1.94 | 14.6 | 10.3 | 0.705:1 | 9.9 |
| Example 2a" | 2.10 | 17.7 | 10.7 | 0.604:1 | 10.1 |
| Example 2b | 1.82 | 7.0 | 4.0 | 0.571:1 | 8.9 |
| Example 2c | 1.83 | 12.1 | 9.1 | 0.752:1 | 9.6 |

Example 3

Activity Testing

A sample of the pellets from Examples 1 and 2 was crushed and 2 ml (0.50 g) of fragments in the sieve range 0.6-1.0 mm were charged to a micro-reactor and reduced to active catalyst in a 2% vol $H_2/N_2$ gas mixture up to 240° C. A methanol synthesis gas of % v/v composition 6.0 CO, 9.2 $CO_2$, 67.0 $H_2$, and 17.8 $N_2$ (R=3.8) was passed over the catalyst at a pressure of 50 barg, temperature 225° C. and space velocity 40000 $h^{-1}$. The outlet methanol was measured on-line using a combination of infrared and gas chromatography systems. Then, for an accelerated life test, the pressure and temperature were raised to above normal operating conditions; these conditions were held to 144 h, then decreased to their former levels, at which the outlet methanol content was measured again.

The relative activities of the catalysts of Examples 1a and 2a', each having a pellet density about 2.0, are given below. The activity quoted is relative to that of a standard oxidic (i.e. a calcined copper-oxide-based catalyst which has been entirely reduced in-situ) having the same Cu:Zn:Mg:Al molar ratio, tested under the same conditions. Measurements were taken at 17 hours on-line and 144 hours on-line. The results were as follows:

| Catalyst    | Time on-line | Relative Activity |
|-------------|--------------|-------------------|
| Example 1a  | 17           | 1.46              |
| Example 2a' | 17           | 1.33              |
| Standard    | 17           | 1.00              |
| Example 1a  | 144          | 1.52              |
| Example 2a' | 144          | 1.42              |
| Standard    | 144          | 1.00              |

The results show superior activity and a lower rate of deactivation for the catalysts used in the process of the present invention compared to a standard oxidic catalysts of the same Cu:Zn:Mg:Al molar ratio.

Example 4 (Comparative)

A catalyst was prepared according to Example 1 of U.S. Pat. No. 4,863,894 (with a molar ratio of Cu:Zn:Al of 59.8:25.6:14.5). The washed material was dried at 110° C. but without a drying step at 180-240° C., and then reduced using a mixture of 5% $H_2$+95% $N_2$ by volume. The reduced powder was passivated and shaped in the same way as Example 1. A range of pellet densities was explored. The MHCS was measured on the as-made pellet and on the pellet after re-reduction to simulate strength in-situ.

| Sample | Pellet Density (g/mL) | MHCS As-Made (kg) | MHCS Re-reduced (kg) | MHCS Ratio | Shrinkage on Reduction (% v/v) |
|--------|-----------------------|-------------------|----------------------|------------|--------------------------------|
| Comparative 4a | 1.70 | 8.1  | 1.7 | 0.210:1 | 16.2 |
| Comparative 4b | 1.83 | 11.4 | 3.7 | 0.325:1 | 19.2 |
| Comparative 4c | 1.88 | 12.3 | 3.8 | 0.309:1 | 19.0 |

While the pelleted material is initially strong, the re-reduction figure shows considerable strength loss and a high shrinkage. High shrinkage is undesirable in catalysts as it is wasteful of reactor volume.

The catalyst (Example 4c) was tested according to the test method set out in Example 3. The relative activity of the catalyst fell to 0.97 at 144 hours.

Example 5

Selectivity Testing

A continuously stirred tank reactor (CSTR) was used to measure the kinetics and deactivation characteristics of the methanol synthesis catalysts of Examples 1 and 2 and a comparative oxide catalyst having the same Cu:Zn:Mg:Al molar ratio. Gas analysis was performed on-line using a combination of infrared and gas chromatography systems. The feed gas composition used was: (% v/v)
CO 6
$CO_2$ 6
$H_2$ 79
$N_2$ 9
R=6.08
Approximately 5 g of whole catalyst pellets were charged to the reactor.

Tests lasted 1 to 8 weeks on a single catalyst charge with the aim to produce information on catalyst activity, stability and selectivity. The initial operational conditions were 225° C. (498° K), 65 barg and mass velocity 80,000 l/hr/kg, reactor space time (W/F) $0.110 \times 10^{-4}$ gm cat./g mol feed/sec. After the initial period, accelerated deactivation at elevated temperatures was carried out. The temperature was cycled to collect comparative data with time on line.

Condensate from exit stream of the reactor was collected and analysed. Analysis was carried out by gas chromatography using calibrated standards as references. The condensate contaminant levels are given below.

|  | Example 1a | Example 2a | Example 2b | Example 2c | Standard Oxidic Material |
|---|---|---|---|---|---|
| Contamination level in condensate (ppm) | | | | | |
| Ethanol             | 170.7 | 212.5 | 227.4 | 154.1 | 378.8 |
| 2-propanol          | 11.3  | 33.3  | 21.9  | 9.0   | 37.8  |
| 1-propanol          | 44.9  | 56.9  | 46.9  | 14.0  | 102.5 |
| Methyl ethyl ketone | 4.3   | 5.6   | nd    | 5.0   | 8.1   |
| 2-butanol           | 24.7  | 61.4  | 49.1  | 27.9  | 82.3  |
| 2 methyl propan-1-ol | 11.6 | 17.9  | 15.3  | nd    | 33.2  |
| 1-butanol           | 10.1  | 16.1  | 10.7  | nd    | 22.9  |
| Total               | 277.6 | 403.6 | 371.3 | 210.0 | 665.6 |
| Percentage of standard catalyst (%) | 41.7 | 60.4 | 55.8 | 31.5 | — | nd—none detected

The results indicate that the catalyst is able to provide a more selective methanol synthesis process that the conventional oxide-based catalyst. In all cases the total by-product level for the pre-reduced catalyst is <405 ppm and the ethanol level <250 ppm.

The invention claimed is:
1. A methanol synthesis process comprising the steps of:
(i) reacting in a synthesis loop a process gas containing hydrogen, carbon dioxide and carbon monoxide over a catalyst comprising shaped units formed from a reduced and passivated catalyst powder, said catalyst powder comprising copper in the range 10-80% by weight, zinc oxide in the range 20-90% by weight, alumina in the range 5-60% by weight, and optionally one or more oxidic promoter compounds selected from the group consisting of compounds of Mg, Cr, Mn, V, Ti, Zr, Ta, Mo, W, Si and rare earths in the range 0.01-10% by weight, to form a product gas, (ii) condensing methanol, water and oxygenate by-products therefrom and (iii) returning unreacted product gas to the synthesis loop, wherein the condensate has a total oxygenate by-product level below 500 ppm.

2. A process according to claim 1 wherein the total oxygenate by-product level is the sum of the ppm weight of ethanol, 2-propanol, 1-propanol, methyl ethyl ketone, 2-butanol, 2-methyl propan-1-ol and -butanol in the recovered condensate.

3. A process according to claim 1 wherein the total oxygenate by-product level is below 400 ppm.

4. A process according to claim 1 wherein the oxygenate by-product has an ethanol content that is ≤300ppm.

5. A process according to claim 1 having a relative condensate purity that is ≤75%.

6. A process according to claim 1 wherein the catalyst comprises magnesium in an amount 1-5% by weight, expressed as MgO.

7. A process according to claim 1 wherein the catalyst has a weight ratio of Cu:Zn expressed as oxide in the range 2:1 to 3.5:1.

8. A process according to claim 1 wherein the alumina in the catalyst is a colloidally-dispersed aluminium oxide or aluminium hydroxide.

9. A process according to claim 1 wherein said catalyst shaped units have a reduced to as-made mean horizontal crush strength ratio of ≥0.5:1 and a copper surface area above 60m$^2$/g Cu.

10. A process according to claim 1 wherein the shaped unit is a pellet formed by compression of the reduced and passivated powder.

11. A process according to claim 10 wherein the catalyst is in the form of a flat-ended cylindrical pellet, ring or trilobe or a domed cylinder having two or more grooves running along a length of the shaped unit.

12. A process according to claim 10 wherein the pellet has a density in the range 1.4 to 2.5 g/cm$^3$.

13. A process according to claim 1 wherein the catalyst has been prepared by the steps comprising:

forming, in an aqueous medium, a composition comprising an intimate mixture of discrete particles of compounds of copper, zinc, aluminium and optionally one or more promoter metal compounds selected from the group consisting of compounds of Mg, Cr, Mn, V, Ti, Zr, Ta, Mo, W, Si and rare earths, (ii) recovering and drying the composition to form a catalyst precursor, (iii) subjecting the dried catalyst precursor composition to reduction conditions so that the copper compounds therein are converted to copper, (iv) passivating the reduced copper surfaces, and (v) shaping the reduced and passivated composition, wherein, prior to the reduction of the copper compounds, the intimate mixture is subjected to a drying step at a temperature in the range 180-240° C.

14. A process according to claim 1 wherein the methanol synthesis process is operated at a temperature in the range 200-320° C.

15. A process according to claim 1 wherein a stoichiometry number, R, as defined by R=(H$_2$-CO$_2$)/(CO+CO$_2$), of the synthesis gas in the loop fed to the catalyst is ≥3.

16. A process according to claim 1 wherein the total oxygenate by-product level is below 300 ppm.

17. A process according to claim 1 wherein the oxygenated by-product has an ethanol content that is ≤250 ppm.

18. A process according to claim 1 having a relative condensate purity that is ≤50%.

19. A process according to claim 10 wherein the catalyst is in the form of a flat-ended cylindrical pellet, ring or trilobe or a domed cylinder having two or more grooves running along a length of the shaped unit, with one or more holes extending there-through.

20. A process according to claim 1 wherein a stoichiometry number, R, as defined by R=(H$_2$-CO$_2$)/(CO+CO$_2$), of the synthesis gas in the loop fed to the catalyst is ≥4.

21. A process according to claim 1 wherein a stoichiometry number, R, as defined by R=(H$_2$-CO$_2$)/(CO+CO$_2$), of the synthesis gas in the loop fed to the catalyst is ≥5.

* * * * *